(12) United States Patent
Takasaki et al.

(10) Patent No.: US 6,175,041 B1
(45) Date of Patent: Jan. 16, 2001

(54) PROCESS FOR PRODUCING TRIFLUOROMETHYLBENZYLAMINES

(75) Inventors: Seiji Takasaki, Saitama; Takahiro Koizumi, Tokyo; Takashi Kume, Saitama; Michio Ishida, Saitama; Satoru Narizuka, Saitama; Eri Tsukada, Saitama, all of (JP)

(73) Assignee: Central Glass Company, Limited, Ube (JP)

( * ) Notice: Under 35 U.S.C. 154(b), the term of this patent shall be extended for 0 days.

(21) Appl. No.: 09/521,009

(22) Filed: Mar. 7, 2000

(30) Foreign Application Priority Data

Mar. 8, 1999 (JP) .................................................. 11-059934

(51) Int. Cl.⁷ .................................................. C07C 209/00
(52) U.S. Cl. .......................... 564/385; 564/389; 564/390; 564/391
(58) Field of Search ................................... 564/385, 389, 564/390, 391

(56) References Cited

U.S. PATENT DOCUMENTS 5,126,497 * 6/1992 Spohn et al. .

* cited by examiner

*Primary Examiner*—Samuel Barts
(74) *Attorney, Agent, or Firm*—Evenson, McKeown, Edwards & Lenahan, P.L.L.C.

(57) ABSTRACT

The invention relates to a process for producing a trifluoromethylbenzylamine represented by the following general formula (1). This process includes hydrogenating a trifliuoromethylbenzonitrile represented by the following general formula (2) by hydrogen in an organic solvent in the presence of ammonia, using a Raney catalyst, (1)

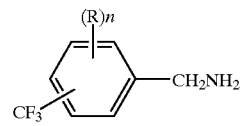

where each R independently represents a halogen selected from the group consisting of fluorine, chlorine, bromine and iodine, an alkyl group having a carbon atom number of 1–4, an alkoxy group having a carbon atom number of 1–4, an amino group, a hydroxyl group or a trifluoromethyl group, and n represents an integer from 0 to 4, (2)

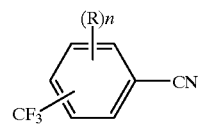

where R and n are defined as above. With this process, it is possible to obtain the trifluoromethylbenzylamine easily and inexpensively at an extremely high yield.

7 Claims, No Drawings

PROCESS FOR PRODUCING TRIFLUOROMETHYLBENZYLAMINES

BACKGROUND OF THE INVENTION

The present invention relates to a process for producing aromatic primary amines having a trifluoromethyl group that are useful in the pharmaceutical and agricultural chemical fields.

Numerous processes for obtaining primary amines by hydrogenation of nitrile compounds have been reported. In addition numerous processes for obtaining primary amines of fluorine-containing aromatics from fluorine-containing aromatic nitrile compounds have also been reported. However, in these known processes, in the case of attempting to obtain primary amines by hydrogenation of nitrile compounds having a trifluoromethyl group, there is a remarkable decrease in selectivity and the following purification steps by distillation and so forth are extremely bothersome, thereby making it difficult to carry out these processes industrially.

Processes for obtaining aromatic primary amines having a trifluoromethyl group from aromatic nitrile compounds having a trifluoromethyl group have problems that remain to be solved, and an industrially useful process for producing aromatic primary amines having a trifluoromethyl group has yet to be established.

SUMMARY OF THE INVENTION

It is therefore an object of the present invention to provide a process for producing a trifluoromethylbenzylamine easily and inexpensively.

According to the present invention, there is provided a process for producing a trifluoromethylbenzylamine represented by the following general formula (1). This process comprises hydrogenating a trifluoromethylbenzonitrile represented by the following general formula (2) by hydrogen in an organic solvent in the presence of ammonia, using a Raney catalyst,

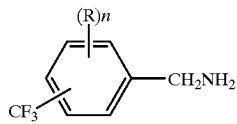

(1)

where each R independently represents a halogen selected from the group consisting of fluorine, chlorine, bromine and iodine, an alkyl group having a carbon atom number of 1–4, an alkoxy group having a carbon atom number of 1–4, an amino group, a hydroxyl group or a trifluoromethyl group, and n represents an integer from 0 to 4,

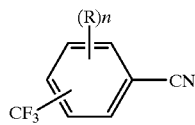

(2)

where R and n are defined as above. With this process, it is possible to obtain the trifluoromethylbentylamine at an extremely high yield.

DESCRIPTION OF THE PREFERRED EMBODIMENTS

The trifluoromethylbenzonitrile represented by the general formula (2) used in the present invention is a benzonitrile having at least one trifluoromethyl group. This benzonitrile may also have a substituent group that is inactive under the conditions of the hydrogenation of the present invention. Examples of such substituent group include halogens (i.e., fluorine, chlorine, bromine and iodine), alkyl groups each having a carbon atom number of 1–4, alkoxy groups each having a carbon atom number of 1–4, amino groups, hydroxyl groups and trifluoromethyl groups. Specific examples of the trifluoromethylbenzonitrile include
2-trifluoromethylbenzonitrile,
3-trifluoromethylbenzonitrile,
4-trifluoromethylbenzonitrile,
2-bromo-5-trifluoromethylbenzonitrile,
2-chloro-5-trifluoromethylbenzonitrile,
2-fluoro-5-trifluoromethylbenzonitrile,
4-iodo-2-trifluoromethylbenzonitrile,
4-iodo-3-trifluoromethylbenzonitrile,
2-methoxy-5-trifluoromethylbenzonitrile,
3-methoxy-4-trifluoromethylbenzonitrile,
4-hydroxy-2-trifluoromethylbenzonitrile,
4-methoxy-3-trifluoromethylbenzonitrile,
2-amino 3-trifluoromethylbenzonitrile,
2-amino-5-trifluoromethylbenzonitrile,
2-amino-6-trifluoromethylbenzonitrile,
3-amino-5-trifluoromethylbenzonitrile,
4-amino-2-trifluoromethylbenzonitrile,
4-amino-3-trifluoromethylbenzonitrile,
2,3-bis(trifluoromethyl)benzonitrile,
2,4-bis(trifluoromethyl)benzonitrile,
2,5-bis(trifluoromethyl)benzonitrile,
2,6-bis(trifluoromethyl)benzonitrile,
3,4-bis(trifluoromethyl)benzonitrile,
3,5-bis(trifluoromethyl)benzonitrile,
2,3,6-tris(trifluoromethyl)benzonitrile,
2,4,6-tris(trifluoromethyl)benzonitrile,
2,3,4,6-tetraquis(trifluoromethyl)benzonitrile,
2-amino-4,6-bis(trifluoromethyl)benzonitrile,
4-amino-3,5-bis(trifluoromethyl)benzonitrile and
4-chloro-3,5-bis(trifluoromethyl)benzonitrile. These trifluoromethylbenzonitriles having trifluoromethyl groups can be produced by various processes. For example, 2-trifluoromethylbenzonitrile can be obtained by fluorinating 2-trifluoromethylbenzonitrile with antimony trifluoride, while 4-trifluoromethylbenzonitrile can be obtained by heating 4-trifluoromethylaniline diazoate with $Ka[Cu(CN)_4]$.

Raney nickel or Raney cobalt can be used as the Raney catalyst in the process of the present invention. Raney catalyst refers to a porous, sponge-like metal catalyst. Although it can be prepared in accordance with routine methods, commercially available catalysts may also be used. Examples of commercially available Raney catalysts include Raney nickel NDT-90 of Kawaken Fine Chemicals Co. and Raney cobalt OFT-55 of Kawaken Fine Chemicals Co. The method for preparing the Raney catalyst is as described in detail in the literature (Kubomatsu, A. and Komatsu, S.: "Raney Catalysts", Kyoritsu Publishing Co. (1971)), and Raney catalysts prepared in accordance with this method can be used in the process of the present invention. In the case of Raney nickel, the catalyst is prepared by adding aluminum, and depending on the case manganese, chromium and/or molybdenum, to nickel (normal content: 40–50 wt %) and developing the alloy with aqueous sodium hydroxide to elute the aluminum. The conditions for development may include a temperature on the order of −20° C. to +120° C., a weight ratio of sodium hydroxide to the nickel-aluminum alloy of 1/1 to 1.5/1, and a treatment time in the range of about 50 minutes to about 12 hours, and these conditions can be suitably combined. In the case of Raney cobalt, the catalyst is prepared by adding aluminum, and depending on the case manganese, chromium and/or molybdenum, to cobalt (normal content: 40–50 wt %) and developing the alloy with aqueous sodium hydroxide to elute the aluminum. The conditions for development may include a temperature on the order of −20° C. to +120° C., a weight ratio of sodium hydroxide to the cobalt-aluminum alloy of 1/1 to 1.5/1, and a treatment time in the range of about 50 minutes to 12 hours, and these conditions can be suitably combined. The amount of Raney catalyst used in the process is preferably 1 to 200 parts by weight, more preferably 5 to 50 parts by weight, to 100 parts by weight of the reaction substrate (i.e., the trifluoromethylbenzonitrile). If the amount is less than 1 part by weight, the reaction may not proceed sufficiently. If the amount exceeds 200 parts by weight, the catalyst may be wasted too much thereby making this undesirable.

The hydrogenation of the present invention preferably uses a non-polar solvent. Examples of non-polar solvents that can be used in the reaction include toluene, xylene, ethylbenzene, tetralin, n-hexane, n-octane, cyclohexane and methylcyclohexane. Although there are no restrictions on the amount of solvent used, the use of roughly 0.1 to 20 parts by weight to 1 part by weight of the trifluoromethylbenzonitrile is preferable in terms of manipulation of the reaction. Deviation from this range, however, does not result in any problems with respect to the reaction.

In general, polar solvents such as methanol have been used for the nitrile hydrogenation solvent. In that case, ammonia is frequently added for the purpose of inhibiting secondary amines formed as a by-product in nitrile hydrogenations. Since the solubility of ammonia is high in these polar solvents, they are also used for reasons of easier workability during charging. However, in the case of the trifluoromethylbenzonitriles of the present invention, polar solvents such as alcohol cause an addition reaction to the trifluoromethylbenzonitriles, and since, for example, methoxyimine is generated in the case of methanol, the use of such polar solvents may result in a significant decrease in yield. Moreover, the reaction products (e.g., methoxyimine) of this addition reaction may turn into dimers and trimers, due to heating and so forth during distillation in following isolation procedures. In contrast, when a non-polar solvent such as toluene is used for the solvent, there is no occurrence of addition of solvent to the starting material, thereby making it possible to obtain the target product (i.e., the trifluoromethylbenzylamine) at high yield.

The process of the present invention can be carried out under pressurization by hydrogen. Upon this, a pressure of 5–250 kg/cm$^2$ is preferable, while that of 10–100 kg/cm$^2$ is more preferable. If the reaction pressure is less than 5 kg/cm$^2$, a longer time is required for reaction. If the reaction pressure exceeds 250 kg/cm$^2$, although there are no problems in terms of the reaction, this is not preferable with respect to the strength of the apparatus, reaction procedure and pressurization procedure.

The process of the present invention can be carried out at −20 to 250° C., and preferably from room temperature to 150° C. Here, room temperature refers to the temperature in the absence of heating or cooling. If the reaction temperature is below −20° C., the reaction requires a longer period of time. If the reaction temperature is above 250° C., the amount of reaction by-products increases and the yield of the target product decreases correspondingly, thus making this undesirable.

In the process of the present invention, the amount of ammonia added is preferably 1–30 parts by weight to 100 parts by weight of the trifluoromethylbenzonitrile as the starting material. Although liquid ammonia is normally used, it may also be introduced as a gas. In addition, basic substance(s) can also be added to the reaction system. Examples of basic substances that can be used include hydroxides, oxides, carbonates and so forth of alkaline metals or alkaline earth metals. Specific examples of such basic substances include sodium hydroxide, potassium hydroxide, lithium hydroxide, calcium hydroxide, magnesium hydroxide, barium hydroxide, sodium carbonate and potassium carbonate. Basic substance(s) can also be added to the reaction system in the form of an aqueous solution prepared to an arbitrary concentration.

The process of the present invention can be carried out either a batch operation or a continuous operation. In the case of using a batch operation, the reaction can be carried out, as follows. At first, predetermined amounts of the trifluoromethylbenzonitrile represented by the general formula (2), Raney catalyst and an organic solvent are charged into a corrosion-resistant, pressure-proof reaction vessel made of stainless steel, glass or having a glass lining. Then, the inside of the reaction vessel is replaced with an inert gas. Then, a predetermined amount of ammonia is added. After that, hydrogen is introduced by adding pressure to a predetermined pressure. Then, the reaction vessel is heated and held at a predetermined temperature with stirring, to carry out the reaction. As the reaction progresses, absorption of hydrogen occurs and the pressure inside the reaction vessel decreases. However, the pressure inside the reaction vessel can be maintained constant by continuously or intermittently introducing hydrogen. After confirming that absorption of hydrogen is no longer occurring, the reaction vessel is cooled, then the contents are removed, and then filtered to separate into an organic matter and the catalyst. The reaction product obtained in this manner is subjected to processing including rinsing with water, drying and distillation in accordance with routine methods, allowing the obtaining of the trifluorobenzylamine of high purity.

The following nonlimitative examples are illustrative of the present invention.

CATALYST PREPARATION EXAMPLE 1

30 g of an alloy powder comprised of nickel and aluminum (nickel: 50 wt %) were charged into 230 g of a 20% aqueous sodium hydroxide solution and then treated for 1 hour at 60–65° C. followed by washing with water several times until the pH of the washing water became 9–10 to obtain a developed nickel (Raney nickel) catalyst.

CATALYST PREPARATION EXAMPLE 2

30 g of an alloy powder comprised of cobalt and aluminum (cobalt: 50 wt %) were charged into 230 g of a 20% aqueous sodium hydroxide solution and then treated for 1 hour at 60–65° C. followed by washing with water several times until the pH of the washing water became 9–10 to obtain a developed cobalt (Raney cobalt) catalyst.

EXAMPLE 1

A 500 ml autoclave equipped with an electromagnetic stirrer was charged with 60 g of 3,5-bis(trifluoromethyl) benzonitrile, 6 g of the developed cobalt catalyst prepared in Catalyst Preparation Example 2, and 262 g of toluene. Then, the autoclave was sealed followed by the introduction of 10 g of liquid ammonia after replacing the inside of the autoclave with nitrogen. Next, after introducing hydrogen to pressurize the autoclave to 40 kg/cm$^2$, the reaction was carried out for 1 hour at a reaction temperature of 100° C. Following completion of the reaction, the reaction vessel was cooled and the reaction liquid was filtered. After separating the catalyst, the resulting organic substance was analyzed by gas chromatography. With this, the yield of 3,5-bis(trifluoromethyl)benzylamine was found to be 98.1%.

EXAMPLE 2

In this example, Example 1 was repeated except in that 6 g of the developed cobalt catalyst was replaced with 6 g of the developed nickel catalyst prepared in Catalyst Preparation Example 1. The yield of 3,5-bis(trifluoromethyl)benzylamine was found to be 95.6%.

EXAMPLE 3

In this example, Example 1 was repeated except in that 262 g of toluene was replaced with 262 g of methanol. The yield of 3,5-bis(trifluoromethyl)benzylamine was found to be 78.8%. A methoxyimine resulting from addition of methanol to 3,5-bis(trifluoromethyl)benzonitrile was recognized as the by-product that caused the decrease in yield.

What is claimed is:

1. A process for producing a trifluoromethylbenzylamine represented by the following general formula (1), said process comprising hydrogenating a trifluoromethylbenzonitrile represented by the following general formula (2) by hydrogen in an organic solvent in the presence of ammonia, using a Raney catalyst, (1)

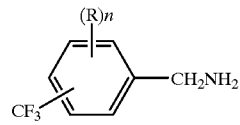

where each R independently represents a halogen selected from the group consisting of fluorine, chlorine, bromine and iodine, an alkyl group having a carbon atom number of 1–4, an alkoxy group having a carbon atom number of 1–4, an amino group, a hydroxyl group or a trifluoromethyl group, and n represents an integer from 0 to 4, (2)

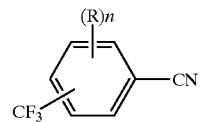

where R and n are defined as above.

2. A process according to claim 1, wherein said Raney catalyst is Raney nickel or Raney cobalt.

3. A process according to claim 1, wherein said organic solvent is a non-polar solvent.

4. A process according to claim 3, wherein said non-polar solvent is selected from the group consisting of toluene, xylene, ethylbenzene, tetralin, n-hexane, n-octane, cyclohexane and methylcyclohexane.

5. A process according to claim 1, wherein said Raney catalyst is in in an amount of from 1 to 200 parts by weight per 100 parts by weight of said trifluoromethylbenzonitrile.

6. A process according to claim 1, wherein said hydrogenating is conducted under a pressurized condition caused by an addition of said hydrogen.

7. A process according to claim 1, wherein said ammonia is in an amount of from 1 to 30 parts by weight per 100 parts by weight of said trifluoromethylbenzonitrile.

* * * * *